United States Patent
Baba

(10) Patent No.: US 9,048,782 B2
(45) Date of Patent: Jun. 2, 2015

(54) EVALUATION METHOD FOR SOLAR MODULE AND MANUFACTURING METHOD FOR SOLAR MODULE

(71) Applicant: Sanyo Electric Co., Ltd., Moriguchi, Osaka (JP)

(72) Inventor: Toshiaki Baba, Kobe (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 72 days.

(21) Appl. No.: 14/056,382

(22) Filed: Oct. 17, 2013

(65) Prior Publication Data
US 2014/0043056 A1 Feb. 13, 2014

Related U.S. Application Data

(63) Continuation of application No. PCT/JP2012/056894, filed on Mar. 16, 2012.

(30) Foreign Application Priority Data

Apr. 28, 2011 (JP) ................. 2011-101368

(51) Int. Cl.
| | |
|---|---|
| *H02S 50/15* | (2014.01) |
| *G01N 21/64* | (2006.01) |
| *G01N 21/66* | (2006.01) |
| *G01N 21/88* | (2006.01) |
| *H01L 31/042* | (2014.01) |
| *G01N 21/95* | (2006.01) |
| *H01L 21/66* | (2006.01) |
| *H02S 50/10* | (2014.01) |

(52) U.S. Cl.
CPC ........... *H02S 50/15* (2014.12); *Y10T 29/49004* (2015.01); *G01N 21/6489* (2013.01); *G01N 21/9501* (2013.01); *H01L 22/34* (2013.01); *H02S 50/10* (2014.12)

(58) Field of Classification Search
CPC ........... G01R 31/2605; G01N 21/6489; G01N 21/9501; H01L 22/34; H02S 50/00–50/15; Y10T 29/49004
See application file for complete search history.

(56) References Cited

U.S. PATENT DOCUMENTS

| | | | | |
|---|---|---|---|---|
| 5,399,504 | A | * 3/1995 | Ohsawa | 438/16 |
| 8,064,054 | B2 | * 11/2011 | Trupke et al. | 356/302 |
| 2009/0297017 | A1 | * 12/2009 | Hudgings et al. | 382/141 |
| 2010/0034455 | A1 | * 2/2010 | Harada et al. | 382/141 |

(Continued)

FOREIGN PATENT DOCUMENTS

| | | |
|---|---|---|
| EP | 2284520 A1 * | 2/2011 |
| JP | H05-041531 A | 2/1993 |

*Primary Examiner* — Huy Q Phan
*Assistant Examiner* — James Split
(74) *Attorney, Agent, or Firm* — Marvin A. Motsenbocker; Mots Law, PLLC

(57) ABSTRACT

Provided is a method for evaluating a solar cell incorporated into a solar module. A PL evaluation step is performed. The PL evaluation step is a step for evaluating the solar cell to be evaluated among a plurality of solar cells (10) by illuminating the solar cell (10) with light from a light source (20) and detecting the intensity of photoluminescent light (L2) emitted by the solar cell (10). The light is irradiated while a light-blocking member (21) is provided between the solar module (1) and the light source (20) so that light from the light source (20) is not incident on portions of the solar module other than the solar cell (10) to be evaluated.

8 Claims, 4 Drawing Sheets

(56) References Cited

U.S. PATENT DOCUMENTS

| | | |
|---|---|---|
| 2010/0182421 A1* | 7/2010 | Chidambaram et al. ...... 348/126 |
| 2011/0117681 A1* | 5/2011 | Bardos et al. ..................... 438/7 |
| 2011/0234790 A1* | 9/2011 | True .............................. 348/126 |
| 2012/0012756 A1* | 1/2012 | Beck et al. ................. 250/459.1 |
| 2012/0126120 A1* | 5/2012 | Fuyuki et al. ................. 250/330 |
| 2012/0248335 A1* | 10/2012 | Kim et al. .................. 250/459.1 |
| 2013/0043405 A1* | 2/2013 | Maxwell et al. ........... 250/459.1 |
| 2013/0062536 A1* | 3/2013 | Bardos et al. .............. 250/459.1 |

\* cited by examiner

EVALUATION METHOD FOR SOLAR MODULE AND MANUFACTURING METHOD FOR SOLAR MODULE

CROSS-REFERENCE TO RELATED APPLICATIONS

This is a continuation of International Application PCT/JP2012/056894, with an international filing date of Mar. 16, 2012, filed by applicant, the disclosure of which is hereby incorporated by reference in its entirety.

FIELD OF THE INVENTION

The present invention relates to an evaluation method for a solar module and a manufacturing method for a solar module.

BACKGROUND

Photoluminescence (PL) techniques, such as those described in Patent Document 1, are known to be used as methods for evaluating solar cells. PL techniques are used to evaluate a solar cell by detecting the PL light that is emitted when a solar cell is illuminated with excitation light.

CITED DOCUMENTS

Patent Documents

Patent Document 1: Laid-Open Patent Publication No. 5-41531

SUMMARY

Problem Solved by the Invention

There is a desire to evaluate solar cells incorporated into a solar module after the solar cells have been modularized to create a solar module.

In view of this situation, it is an object of the present invention to provide a method for evaluating solar cells incorporated into a solar module.

Means of Solving the Problem

The evaluation method for a solar cell according to the present invention is an evaluation method for a solar module including a plurality of solar cells. The evaluation method for a solar cell according to the present invention includes a PL evaluation step. The PL evaluation step is a step for evaluating the solar cell to be evaluated among a plurality of solar cells by illuminating the solar cell with light from a light source and detecting the intensity of photoluminescent light emitted by the solar cell. The light is irradiated while a light-blocking member is provided between the solar module and the light source so that light from the light source is not incident on portions of the solar module other than the solar cell to be evaluated.

The method for manufacturing a solar module according to the present invention includes a step for evaluating the solar module by means of the evaluation method of the solar cell according to the present invention.

Effect of the Invention

The present invention is able to provide a method for evaluating solar cells incorporated into a solar module.

DETAILED DESCRIPTION

Figure 1:
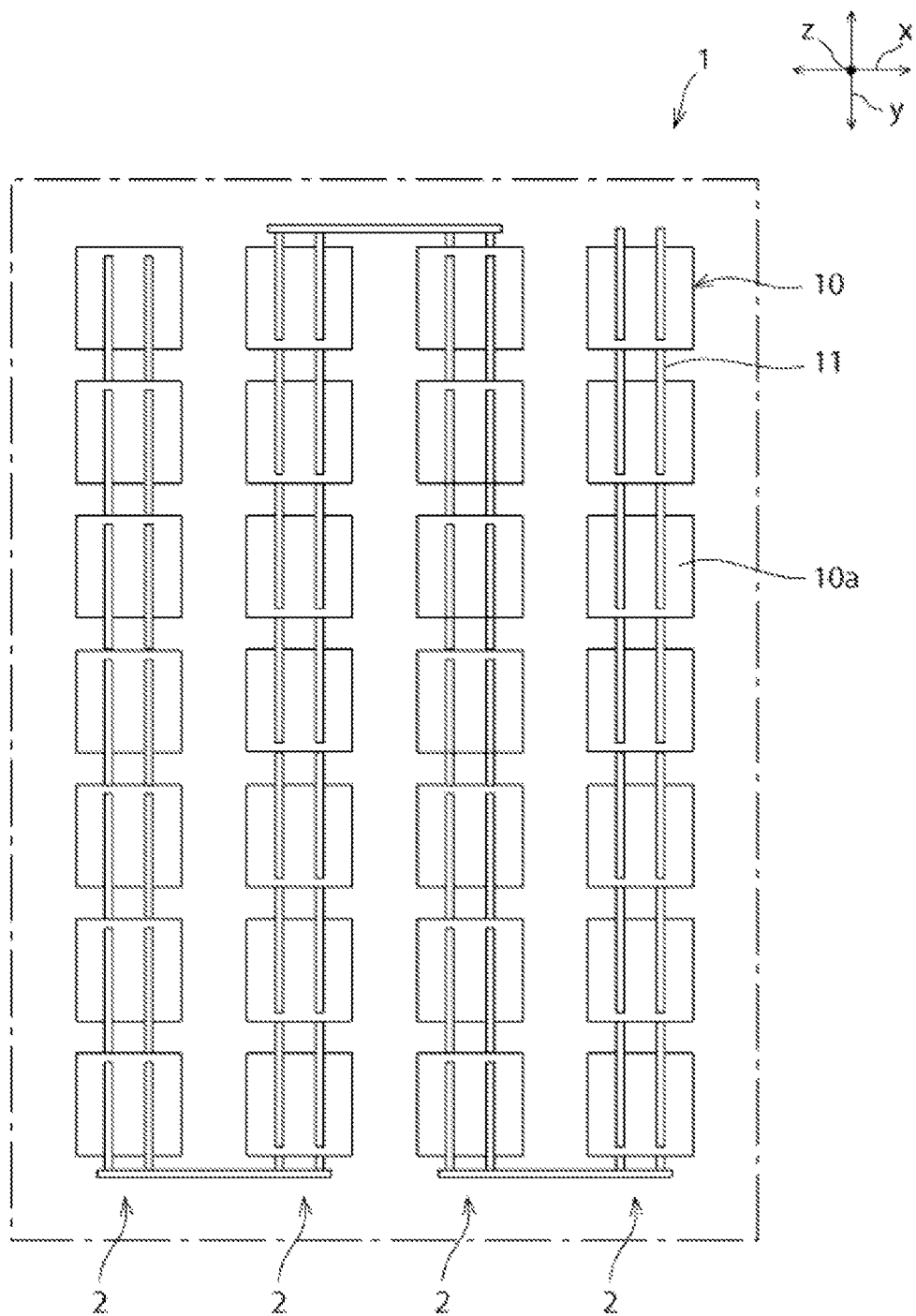
FIG. 1 is a schematic plan view of a solar module according to an embodiment.

The following is an explanation of examples of preferred embodiments of the present invention. The following embodiments are merely examples. The present invention is not limited to the following embodiments in any way.

Further, in each of the drawings referenced in the embodiments, members having substantially the same function are denoted by the same symbols. The drawings referenced in the embodiments are also depicted schematically. The dimensional ratios of the objects depicted in the drawings may differ from those of the actual objects. The dimensional ratios of objects may also vary between drawings. The specific dimensional ratios of the objects should be determined with reference to the following explanation.

Configuration of Solar Module 1

Figure 2:
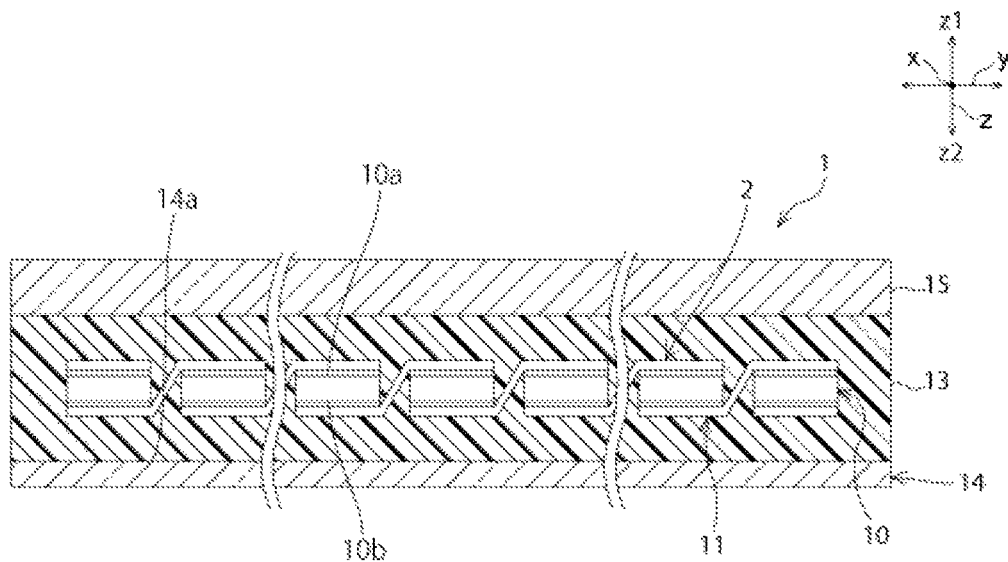
FIG. 2 is a schematic cross-sectional view of a solar module according to an embodiment.

FIG. 1 is a schematic plan view of a solar module according to an embodiment, and FIG. 2 is a schematic cross-sectional view of a solar module according to the embodiment.

The solar module 1 includes a plurality of solar cell strings 2. The solar cell strings 2 are arranged at intervals from each other in one direction (the x direction). A solar cell string 2 has a plurality of solar cells 10. In a solar cell string 2, the solar cells 10 are arranged at intervals from each other in a direction (the y direction) perpendicular to the previous direction (x direction). Thus, the solar cells 10 in the solar module 1 are arranged at intervals from each other in a matrix in both the x direction and the y direction.

The solar cells 10 constituting the solar cell strings 2 are connected to each other electrically by a wiring member 11. The wiring member 11 and solar cells 10 can be bonded using a resin adhesive or solder.

Each solar cell 10 has a light-receiving surface 10$a$ and a back surface 10$b$. Here, the main surface on which light is directly incident is the light-receiving surface 10$a$, and the other main surface is the back surface 10$b$. However, each solar cell 10 can receive light and generate electricity on both the light-receiving surface 10$a$ and the back surface 10$b$. In other words, the solar cells 10 are bifacial light-receiving solar cells.

There are no particular restrictions on the solar cells 10. They can be configured, for example, as single-crystal silicon solar cells, polycrystalline silicon solar cells, thin-film silicon solar cells, compound semiconductor solar cells, dye-sensitized solar cells, and organic thin-film solar cells. The solar cells 10 do not have to generate electricity when light is received on the back surface 10$b$.

A transparent member 15 is arranged on the light-receiving surface side (z1 side) of the solar cells 10. In other words, the transparent member 15 is arranged on the side of the solar cells 10 with the light-receiving surface 10$a$. The transparent member 15 transmits light with a wavelength contributing to the generation of electricity in the solar cells 10.

There are no particular restrictions on the constituent material of the transparent member 15. The transparent member 15 can be, for example, a glass plate or a plastic plate.

A reflective member 14 is arranged on the back surface side (z2 side) of the solar cells 10. In other words, the reflective member 14 is arranged on the side of the solar cells 10 with the back surface 10b. The reflective member 14 is a member which reflects light with a wavelength contributing to the generation of electricity in the solar cells 10. The reflective member 14 is constituted so that at least the surface arranged on the solar cell 10 side has reflective properties. In other words, the reflective member 14 has a reflective surface 14a at least on the solar cell 10 side that reflects light with a wavelength contributing to the generation of electricity in the solar cells 10.

There are no particular restrictions on the constituent materials of the reflective member 14. The reflective member 14, for example, can be constituted as a member in which weather-resistant film, a reflective layer and transparent film are stacked in order from the side opposite that of the solar cell 10. The reflective member 14 can also be constituted, for example, as a member in which weather-resistant film and a reflective layer are stacked in order from the side opposite that of the solar cell 10. The reflective layer can be metal, an alloy material or a white resin film. An adhesive layer may be provided between the weather-resistant film and reflective layer, and between the reflective layer and the transparent film. The weather-resistant film, reflective layer and transparent film may have a single-layer structure or multilayer structure.

A bonding layer 13 is provided between the transparent member 15 and the reflective member 14. A plurality of solar cell strings 2 are arranged inside the bonding layer 13. The bonding layer 13 transmits light with a wavelength contributing to the generation of electricity in the solar cells 10.

There are no particular restrictions on the constituent materials of the bonding layer 13 as long as the material transmits light with a wavelength contributing to the generation of electricity in the solar cells 10. The bonding layer 13 can be constituted, for example, of an ethylene-vinyl acetate (EVA) copolymer.

Method of Manufacturing Solar Module

The following is an explanation of an example of a manufacturing method for solar modules 1.

First, a solar module 1 is created. There are no particular restrictions on the method used to create the solar module 1. The solar module 1 can be created using any well-known method.

Next, the evaluation step is performed. The evaluation step is a step in which the solar module 1 is evaluated to determine whether or not there are any defective solar cells or defective electrical connections in the solar module 1. Defective solar cells include solar cells having a defective semiconductor junction such as a pn junction or pin junction.

After the evaluation step has been performed, a sorting step may be performed to sort solar modules 1 that were free of defective solar cells in the evaluation step. A subsequent step may also be performed to discard or reuse solar modules 1 determined to have a defective solar cell in the evaluation step.

The evaluation step includes at least a PL evaluation step. In the embodiment described below, the evaluation step includes both an EL (electroluminescence) evaluation step and a PL evaluation step. The EL evaluation step is performed first.

EL Evaluation Step

The EL evaluation step is a step in which solar cells 10 are evaluated by supplying electric power to a solar module 1 and detecting the intensity of the electroluminescent light (EL light) emitted by at least one of the solar cells 10 in the solar module 1.

For example, when at least a portion of the wiring member 11 has become delaminated from a solar cell 10 and the solar cell does not receive sufficient power, either EL light is not emitted or EL light is emitted at low intensity from the solar cell. Also, when sufficient power is supplied to a solar cell but the solar cell has a defect such as a semiconductor junction defect, either EL light is not emitted or EL light is emitted at low intensity from the solar cell. Therefore, by supplying electric power to a solar module 1 and detecting the intensity of the EL light emitted by the solar cells 10 in the solar module 1, the presence of defects, such as electrical connection defects and junction defects, in solar cells 10 can be determined all at once.

When, as a result of the EL evaluation, all of the solar cells 10 in a solar module 1 emit EL light and the intensity of none of the EL light is low, a solar module 1 can be determined to be free of defective solar cells 10. However, when a solar cell included in a solar module 1 does not emit EL light or emits EL light at low intensity, a solar module 1 can be determined to have a defective solar cell 10. In the EL evaluation step, a solar module 1 is determined to be a normal solar module when it has been evaluated and deemed free of defective solar cells 10. A solar module 1 evaluated and deemed to have a defective solar cell 10 in the EL evaluation step is relegated to the PL evaluation step.

In the EL evaluation step, sufficiently intense EL light will not be emitted from a defective cell 10 regardless of the cause of the defect. Even though a defective solar cell 10 can be detected in the EL evaluation step, it is difficult to determine whether the defect is due to a faulty electrical connection or a faulty semiconductor junction. Therefore, a PL evaluation step is performed after the EL evaluation step.

PL Evaluation Step

Figure 3:
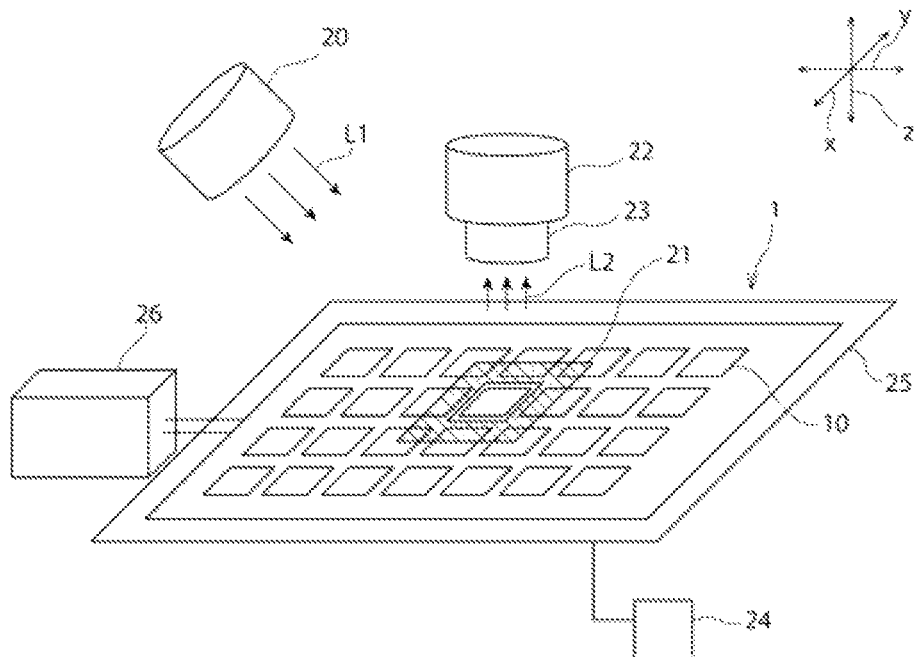
FIG. 3 is a schematic side perspective view used to explain a PL evaluation step according to an embodiment.
Figure 4:
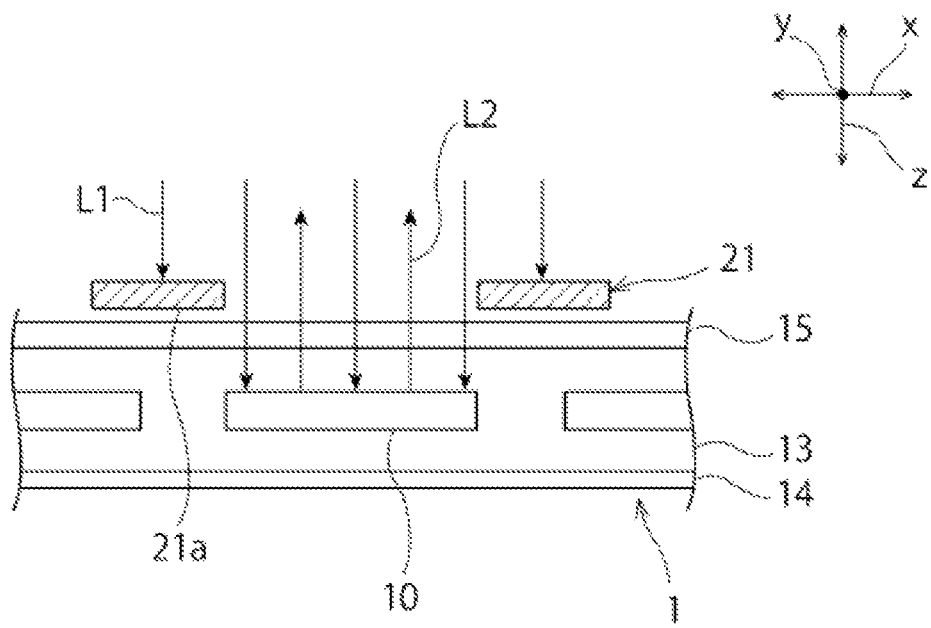
FIG. 4 is a schematic side cross-sectional view used to explain a PL evaluation step according to an embodiment.

FIG. 3 is a schematic side perspective view used to explain a PL evaluation step according to an embodiment, and FIG. 4 is a schematic side cross-sectional view used to explain a PL evaluation step according to an embodiment.

In the present invention, the PL evaluation step is performed on solar modules 1 that have been discovered to have a defect. In the PL evaluation step, any solar cell 10 deemed to be defective among the solar cells 10 of a solar module 1 in which a defect has been discovered is illuminated by a light source 20, and the intensity L2 of the photoluminescent light (PL light) emitted by the solar cell 10 is detected in order to evaluate the solar cell 10. Preferably, the light source 20 is arranged so as to be able to illuminate an entire solar cell 10 with uniform light at an energy level greater than the bandgap of the photoactive layer in the solar cell 10. The light source 20 can be configured using, for example, a light-emitting diode (LED) or laser element.

The intensity of the light L1 emitted from the light source 20 is preferably from 0.01 suns to 1 sun depending on the solar cell characteristics. Here, 1 sun has a photon flux of approximately $2.9 \times 10^{17}/cm^2 \cdot s$.

More specifically, a solar cell 10 found to have a defect in the EL evaluation step (because EL light of a sufficiently high intensity is not emitted) is illuminated by the light source 20, and the intensity of the PL light emitted by the solar cell 10 is detected and evaluated.

In the PL evaluation step, when a solar cell 10 illuminated by excitation light has a defect internal to the solar cell 10 such as a semiconductor junction defect, the intensity of the detected PL light L2 is lowered. When the solar cell 10 itself is not defective and the defect is an electrical connection defect caused, for example, by a delaminated wiring member 11, the intensity of the PL light L2 is not lowered. Therefore, by performing a PL evaluation step after the EL evaluation step, the defect can be identified as being either a defect internal to the solar cell 10 or an electrical connection defect.

When a solar cell 10 evaluated in the PL evaluation step is determined to have an internal defect such as a semiconductor junction defect, the solar cell 10 cannot be reused. Therefore, a solar cell 10 deemed to be defective in the PL evaluation step is discarded. Solar cells 10 deemed to be normal in the PL evaluation step do not to have any internal defects, and therefore the solar cell 10 can be reused. Solar cells 10 deemed to be normal in the PL evaluation step, among the solar cells 10 of a solar module 1 deemed to be defective in the EL evaluation step, are removed from the solar module 1 and stored for reuse.

When the PL evaluation step is performed before the EL evaluation step, defects internal to a solar cell 10 and electrical connection defects can be identified. However, in this case, the PL evaluation step has to be performed on all of the solar cells 10 in the solar module 1. In other words, the PL evaluation step has to be performed the same number of times as the number of solar cells 10 in the solar module 1.

In the present embodiment, the PL evaluation step is performed only on solar cells 10 from which EL light of sufficient intensity was not detected in the EL evaluation step. Also, the EL evaluation step can be performed simultaneously on multiple solar cells 10 in a solar module 1. Thus, the present embodiment reduces the number of times the PL evaluation step has to be performed. This can improve the manufacturing efficiency of solar modules 1.

When another solar cell 10 is to be evaluated after the evaluation of a solar cell 10 has been completed, a displacement mechanism 24 displaces the table 25 on which the solar module 1 has been placed in both direction x and direction y, in order to displace the table 25 and the solar module 1 placed on the table 25 with respect to the light source 20, the detector 22, a filter 23 and a light-blocking member 21.

The following is a more detailed explanation of the PL evaluation step. In the present embodiment, illumination is performed by the light source 20 with a light-blocking member 21 arranged between the solar module 1 and the light source 20 on the optical path of the light L1 so that the light L1 from the light source 20 is not incident on portions of the module other than the solar cell 10 to be illuminated.

Figure 5:
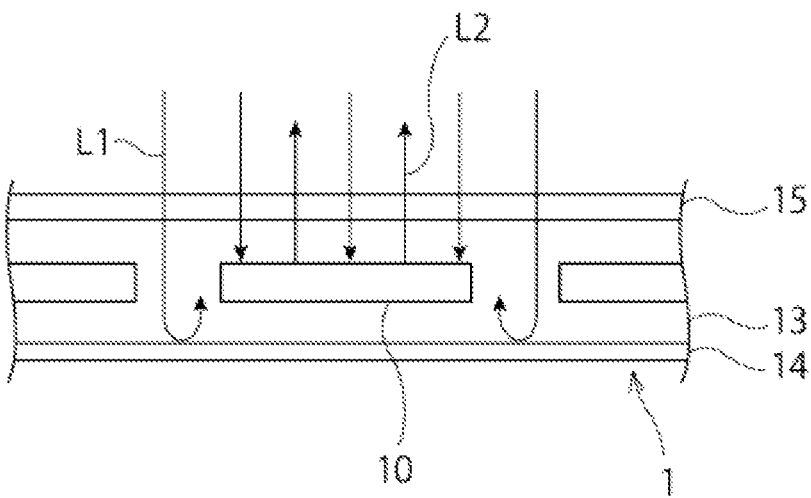
FIG. 5 is a schematic cross-sectional view used to explain the PL evaluation step in a reference example.

When a light-blocking member 21 is not arranged in this manner, as shown in FIG. 5, light L1 from the light source 20 is incident on portions of the module other than the solar cell 10 to be illuminated. When the light L1 is incident on adjacent solar cells 10, the light L1 is reflected towards the solar cells 10 in the reflective surface 14a of the reflective member 14. This reflected light is again reflected, for example, by the surface of the transparent member 15 facing the solar cells 10 and is incident on the solar cells 10. Therefore, when a light-blocking member 21 is not provided, light that is not directly incident on the solar cell 10 becomes incident on the solar cell 10. Thus, the amount of light incident on the solar cell 10 exceeds the desired level, and the amount of PL light L2 increases relative to the increased amount of incident light. As a result, the characteristics of solar cells 10 cannot be evaluated properly.

In the present embodiment, the light-blocking member 21, as mentioned above, suppresses light from the light source 20 becoming incident on the portions of the module other than the solar cell 10 to be illuminated. Therefore, only directly incident light is incident on the solar cell 10. As a result, the characteristics of the solar cell 10 can be evaluated more accurately.

Also, in the present embodiment, the surface 21 of the light-blocking member 21 facing the solar module 1 is a light-absorbing surface which absorbs light L1 from the light source 20. This can control light L1, which has been reflected by the surface of the transparent member 15 opposite the solar cells 10, from being reflected by the surface 21a of the light-blocking member 21 and becoming incident on the solar cells 10. As a result, the characteristics of the solar cell 10 can be evaluated more accurately.

This surface 21a of the light-blocking member 21 can be made into a light-absorbing surface by making the light-blocking member 21 out of a light-absorbing material such as a black material, or by providing a light-absorbing layer on the surface of the light-blocking member 21. The light-absorbing layer can be formed using, for example, black paint.

In the present embodiment, illumination is performed so that the plane formed by the optical axis of the light L1 emitted by the light source 20 and the direction in which the wiring member 11 extends (the y direction) is perpendicular to the light-receiving surface 10a of the solar cell 10. When illumination is performed while the plane formed by the optical axis of the light L1 and the x direction perpendicular to the direction in which the wiring member extends is not perpendicular to the light-receiving surface 10a of the solar cell 10, the light L1 is less likely to be blocked by the wiring member 11. Thus, the light L1 is able to illuminate more of the light-receiving surface 10a of the solar cell 10. As a result, the characteristics of the solar cell 10 can be evaluated more accurately.

In the solar module 1, the transparent member 15 is arranged on the light-receiving surface 10a of the solar cell 10. Thus, light L1 from the light source 20 is often reflected by the surface of the transparent member 15 and becomes incident on the detector 22 detecting the intensity of the PL light L2. When the detector 22 is sensitive to light L1 in addition PL light L2, the detector 22 cannot detect the amount of PL light L2 accurately.

In the present embodiment, the intensity of the PL light L2 is detected by a detector 22 for detecting the PL light L2 via a filter 23 arranged between the detector 22 and the solar cell 10 on the optical path of the PL light L2. This filter transmits PL light L2 but not light L1 from the light source 20. As a result, the influence of reflected L1 light is eliminated, and the intensity of PL light L2 can be measured more accurately. As a result, the characteristics of the solar cell 10 can be evaluated more accurately.

The detector 22 can be configured from imaging elements such as a charge-coupled device (CCD) or complementary metal-oxide semiconductor device (CMOS). A cooling device is preferably provided for the detector 22. When the temperature of the detector 22 is held constant by a cooling device, fluctuations in quantum efficiency can be suppressed.

Because the wavelength of PL light L2 emitted by a crystalline silicon solar cell is from 900 nm to 1200 nm, the wavelength of the light L1 emitted by the light source 20 is preferably 850 nm or less to enable the light L1 from the light source 20 to be differentiated from the PL light L2. In this case, the filter 23 can be a band-pass filter or a long-pass filter which blocks light with a wavelength of 950 nm or less.

In the present embodiment, the PL evaluation step is performed with the solar module 1 in an electrically open state. As a result, the influence on solar cells 10 connected to a solar cell 10 being evaluated can be eliminated, and the characteristics of the solar cells 10 can be evaluated more accurately.

As mentioned above, the PL evaluation step can be used to perform an evaluation other than an evaluation for the presence of solar cells 10 having a defect. For example, the PL evaluation step can be used to evaluate the open-circuit voltage (Voc) of an illuminated solar cell by measuring the open-circuit voltage of the solar module 1 using a voltage detector 26.

By measuring the intensity distribution of PL light L2 in a solar cell 10, the open-circuit voltage distribution of the solar cell 10 can also be obtained on the basis of Equation (1) below.

$$Voc(x, y) = (kT/q) \cdot \ln\{Ipx(x, y)/c\} \quad (1)$$

Provided that,
Voc (x, y): Open-circuit voltage at coordinate (x, y)
Ipx (x, y): Intensity of PL light L2 at coordinate (x, y)
k: Boltzmann's constant
T: Absolute temperature
q: Elementary charge
c: Constant When the intensity of the light L1 from the light source 20 is changed multiple times and the intensity of the PL light L2 is measured, the open-circuit voltage distribution of a solar cell 10 relative to the intensity of the light L1 from the light source can be obtained from Equation (1).

Figure 6:
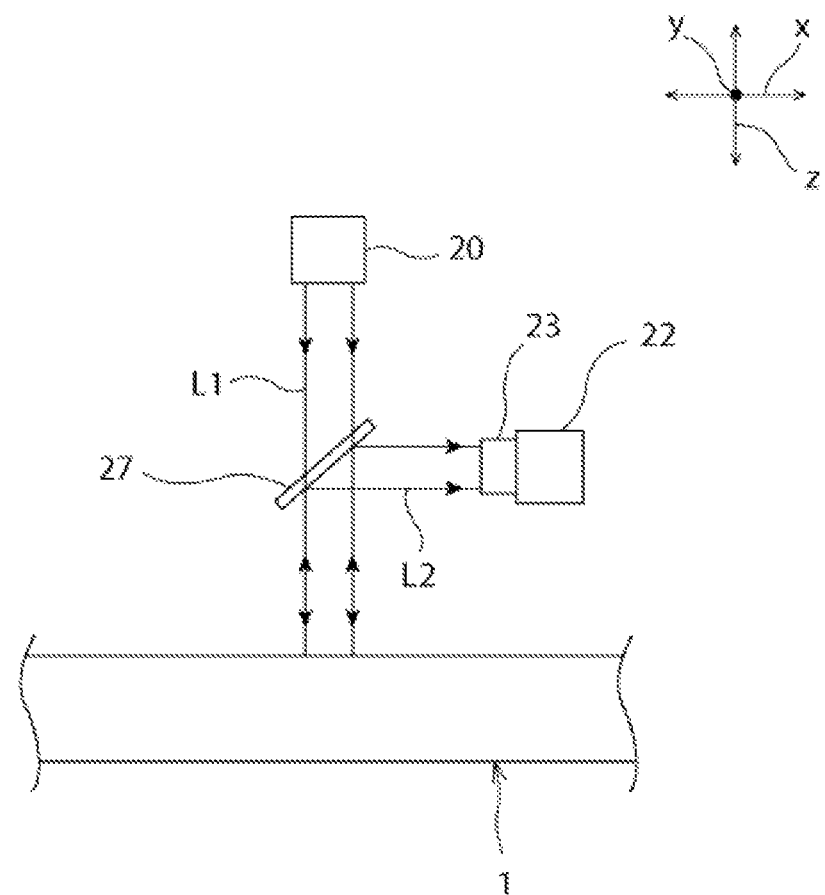
FIG. 6 is a schematic cross-sectional view used to explain the PL evaluation step in a modified example.

The present invention includes many other embodiments not described herein. For example, in the explanation of the example in the first embodiment, the solar cell 10 is illuminated from a direction that is parallel to the y direction and is inclined with respect to the z direction. However, as shown in FIG. 6, the light may be emitted perpendicular to the solar cell 10. In this situation, the light L1 from a light source 20 may be reflected by a dichroic mirror 27 arranged between the light source 20 and the solar module 1 to reflect the PL light L2 and reflect and thereby direct only the PL light L2 to the detector 22.

In the explanation of the example in the first embodiment, the manufacturing process for a solar module 1 includes both a PL evaluation step and an EL evaluation step. However, the PL evaluation step and EL evaluation step may be performed separately from the manufacturing process for a solar module 1. In the present invention, at minimum the PL evaluation step should be performed.

In the explanation of the example in the first embodiment, the light-blocking member 21 was arranged on the solar module 1. However, the light-blocking member 21 may be arranged in front of the light source 20.

The present invention includes many other embodiments not described herein. Therefore, the technical scope of the present invention is defined solely by the items of the invention specified in the claims pertinent to the above explanation.

KEY TO THE DRAWINGS

1: Solar module
10: Solar cell
10a: Light-receiving surface
10b: Back surface
11: Wiring member
13: Bonding layer
14: Reflective member
14a: Reflective surface
15: Transparent member
20: Light source
21: Light-blocking member
21a: Surface
22: Detector
23: Filter
26: Voltage measuring device
27: Dichroic mirror
L1: Light from light source
L2: PL light

What is claimed is:

1. A method for evaluating a solar module having a plurality of solar cells,
    the method comprising a PL evaluation step for evaluating a solar cell to be evaluated among the plurality of solar cells by illuminating the solar cell from a light source and detecting the intensity of photoluminescent light emitted by the solar cell,
    the light being illuminated while a light-blocking member is arranged between the solar module and the light source so light from the light source is not incident on portions of the solar module other than the solar cell to be evaluated.

2. The method for evaluating a solar module according to claim 1, wherein the surface of the light-blocking member on the solar module side is a light-absorbing surface for absorbing light from the light source.

3. The method for evaluating a solar module according to claim 1, wherein light from the light source is blocked between the solar cell and a detector for detecting the intensity of the photoluminescent light, the intensity of the photoluminescent light being detected by the detector via an interposed filter transmitting the photoluminescent light.

4. The method for evaluating a solar module according to claim 1, further comprising an EL evaluation step for evaluating the solar cell by supplying electric power to the solar module and detecting the intensity of the electroluminescent light emitted by the solar cell.

5. The method for evaluating a solar module according to claim 4, wherein the PL evaluation step is performed after the EL evaluation step.

6. The method for evaluating a solar module according to claim 5, wherein the PL evaluation step is performed on a solar cell when it is evaluated that a defect is present in the EL evaluation step.

7. A method for manufacturing a solar module comprising a step for evaluating the solar module using the evaluation method according to claim 1.

8. The method for manufacturing a solar module according to claim 7, further comprising a step for removing from the solar module and reusing a solar cell evaluated as normal by the PL evaluation step.

* * * * *